United States Patent [19]

Zdunek et al.

[11] Patent Number: 5,164,321
[45] Date of Patent: Nov. 17, 1992

[54] PROCESS FOR THE REMOVAL OF NON-SPECIFIC TURBIDITIES

[75] Inventors: Dietmar Zdunek; Friederike Weber, both of München, Fed. Rep. of Germany

[73] Assignee: Boehringer Mannheim GmbH, Mannheim, Fed. Rep. of Germany

[21] Appl. No.: 464,618

[22] Filed: Jan. 3, 1990

Related U.S. Application Data

[63] Continuation-in-part of Ser. No. 222,499, Jul. 21, 1988, abandoned.

[30] Foreign Application Priority Data

Jul. 31, 1987 [DE] Fed. Rep. of Germany ....... 3725475

[51] Int. Cl.$^5$ .................. G01N 33/536; G01N 33/539
[52] U.S. Cl. .................................... 436/536; 436/533; 436/534; 436/17; 436/18; 436/174; 436/175; 436/825; 436/826; 436/909; 436/539
[58] Field of Search .................... 435/7.1, 188; 436/17, 436/18, 174, 175, 501, 533, 534, 536, 825, 826, 909

[56] References Cited

U.S. PATENT DOCUMENTS

| | | | |
|---|---|---|---|
| 4,600,698 | 7/1986 | Toth | 436/534 |
| 4,649,120 | 3/1987 | Stever | 436/13 |
| 4,704,365 | 11/1987 | Yost | 435/188 |
| 4,743,561 | 5/1988 | Shaffar | 436/501 |
| 4,760,030 | 7/1988 | Peterson et al. | 436/509 |

FOREIGN PATENT DOCUMENTS 0141879  5/1985  European Pat. Off. .

OTHER PUBLICATIONS

Windholz, M., editor, *The Merck Index*, 9th edition (Merck and Co., Inc, Rahway, N.J.), 1976, p. 1110.

*Primary Examiner*—Esther L. Kepplinger
*Assistant Examiner*—Toni Scheiner
*Attorney, Agent, or Firm*—Felfe & Lynch

[57] ABSTRACT

A process for the removal of non-specific turbidities in the carrying out of determinations according to the immuno-assay principle, wherein an inorganic boron compound is added to the sample solution in combination with a buffer system.

5 Claims, 1 Drawing Sheet

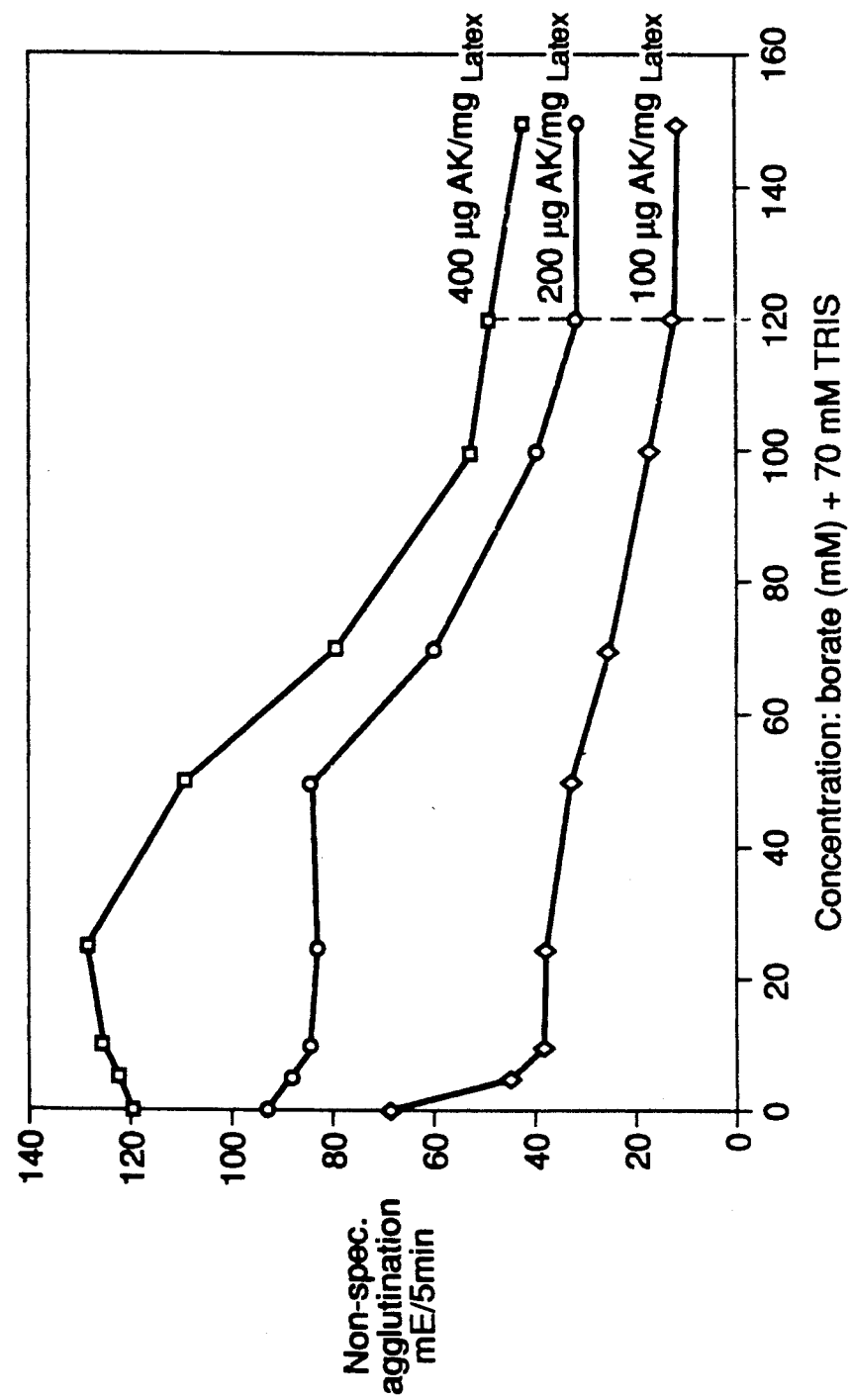

PROCESS FOR THE REMOVAL OF NON-SPECIFIC TURBIDITIES

This is a continuation-in-part of application Ser. No. 222,499 filed on Jul 21, 1988, now abandoned.

BACKGROUND OF THE INVENTION

The present invention is concerned with a process for the removal of non-specific turbidities in the carrying out of determinations according to the immunoassay principle.

The development of determinations according to the immuno-assay principle has led to a decisive improvement in the sensitivity and selectivity in the case of the determination of specifically bindable substances, such as proteins, haptens and antibodies, and has, therefore, achieved great importance in clinical chemical laboratories. The further development of these methods starting from the radio-immunoassay led not only to the broadening of the available labelling methods but also to the development of various analysis techniques. Immuno-assays which use enzymes and fluorescing compounds as labellings are today widely used. The determination of the labelling, and thus of the substance to be detected thereby, depends upon a change of absorption or emission of light to be measured photometrically. It is a basic requirement of these processes that they provide a measurement signal which is directly proportional to the amount of the substance to be determined but, at the same time, a disturbance by components which are present in the solution to be investigated, for example serum, must be avoided with certainty. In addition, they must display a very high sensitivity so that sufficiently precise results can be achieved even in the picomole range. By means of these new determination processes, it became possible to detect substances in serum, the detection of which was not possible at all with the previously known analytical processes.

In the case of the detection of these substances present in very small amounts, for example TSH or AFP, it is naturally especially important to exclude all disturbances which lead to a falsification of the result. In the case of the determination of clinical parameters in serum samples or in standards which are prepared on the basis of serum, disturbances frequently occur due to non-specific agglutination. This non-specific agglutination leads to more or less slight turbidities which disturb the photometric evaluation. Hitherto, these non-specific agglutinations could not be completely eliminated either by the addition of chaotropic reagents or by the addition of detergents.

Therefore, it is an object of the present invention to provide a process for suppressing or dissolving non-specific agglutinations in serum samples.

SUMMARY OF THE INVENTION

Thus, according to the present invention, there is provided a process for the removal of non-specific turbidities in the carrying out of determinations according to the immuno-assay principle, wherein an inorganic boron compound is added to the sample in combination with a buffer system.

Surprisingly, by means of the use of a combination of the two additives according to the present invention, the non-specific agglutination is completely suppressed so that, in the case of the photometric determination of substances which are present in serum in extremely low concentrations, disturbances no longer occur.

BRIEF DESCRIPTION OF THE DRAWING

The attached drawing is a graph showing the results of Example 3.

DETAILED DISCLOSURE

In the carrying out of determinations according to the immuno-assay principle, which are per se known, the present invention provides for adding to the sample solution a combination of an inorganic boron compound and a buffer system. Non-specific turbidities can thereby be removed. The addition of the substances used according to the present invention takes place before the photometric measurement. They can be added together with the reagents used for carrying out the immuno-assay or alternatively, can be added previously to the serum or after the addition of the reagents. The only thing that is important is that the removal of the turbidity take place before carrying out the photometric determination.

An essential component is an inorganic boron compound. There are a large number of compounds which can be used according to the present invention. The inorganic derivatives of boric acid are preferably used since they are commercially available and stable and are soluble in the reaction system. Borates, metaborates, tetraborates and perborates in the form, of their alkali metal salts and preferably of their sodium salts are especially preferred.

The borates, metaborates and tetraborates are suitable for all immuno-assays. Perborate as boron compound is very effective but it should only be used in immuno-assays in which oxidation-stable antibodies are used. In the case of immuno-assays in which oxidation-sensitive antibodies have to be used, for example the TSH antibodies, the antibody reaction is influenced by the addition of the perborate. The TSH antibody is oxidation-sensitive to the $H_2O_2$ contained in the perborate and a portion of the TSH antibodies is destroyed by the proxide. Since fewer antibodies would be available for the immunological reaction, the sensitivity of the immunological reaction decreases. However, it is still possible to carry out a TSH determination and to eliminate the non-specific agglutinations by use of the perborate but, for the sake of sensitivity of the immuno-assay, it is preferable to use another boron compound.

The inorganic boron compound is preferably used in a concentration of 100 to 150 mmole/liter. Less than 100 mmole/liter of borate is used, under certain circumstances the removal of the turbidity is no longer optimal although lower concentrations can in some cases produce satisfactory results. An amount of more than 150 mmole/ liter of borate does not provide any further improvement so that it is not expedient to use higher concentrations.

As second component, there is added to the sample solution a buffer system other than a borate buffer. There can be used the buffer systems known for immunological processes. It is preferable to use a zwittionic buffer system of the type disclosed by Good in Biochemistry 5:467–77 (1966), such as TRIS or HEPES buffer. According to the present invention, TRIS buffer is especially preferably used.

The buffer system is used in a concentration of 70 to 100 mmole/liter. Lower concentrations do not give an optimum result, whereas more than 100 mmole/liter of buffer does not provide any further improvement.

The process according to the present invention can be used for all types of immuno-assays in which a photometric determination takes place, such as ELISA and LPIA. The process according to the present invention is especially suitable for the detection of substances which are present in very low concentrations.

The following Examples are given for the purpose of illustrating the present invention:

EXAMPLE 1

Immuno-assays for the determination of AFP were carried out with the use of various buffer substances and of various boron compounds. The following reagents were used:

Reagent 1

100 mmole/liter buffer, pH 7.5
20 120 mmole/liter boron compound
2% by weight of polyethylene glycol with an average molecular weight of about 6000 (PEG 6000)
0.5% by weight Pluronic F68 (tenside based on alkylene oxide; Poloxamer)
1% by weight bovine serum albumin. The boron compounds used were boric acid, sodium tetraborate ($Na_2B_4O_7$) sodium metaborate ($NaBO_2 \times 4-H_2O$) and sodium perborate ($NaBO_2 \times H_2O_2 \times 3-H_2O$).

As reagent 2, there was used a latex particle dispersion which was prepared according to the carbodiimide method, such as is described in J. Ex. Med., 154-1, 1539-1553/1981; U.S. Pat. Specification No. 3,857,931, as well as J. Immunol. Meth., 22, 165-174/1978. For this purpose, polystyrene particles which had a diameter of from 70 to 300 nm. and contained activated carboxyl groups were reacted with polyclonal antibodies against AFP with a loading density of 3 to 400 µg. of antibodies per mg. of latex, depending upon the particle size. Subsequently, washing was carried out three times in 200 mmole/liter glycine buffer (pH 7.5) + 1% bovine serum albumin, followed by centrifuging. In each case, 80 µl. of a dispersion of 0.35% by weight of these latex particles were used in 200 mmole/liter of glycine buffer (pH 7.5).

As sample, there was used human serum standard which was free of analyte. 80 pl. of In each case, 860 µl. of reagent 1 and 100 µpl. of sample were mixed together at 37° C. and the blank value determined at 623 nm. Subsequently, 80 µl. of reagent 2 were added thereto and, after 5 minutes, the turbidity was measured at 623 nm. The results obtained are given in the following Table I.

| Example: AFP determination Concentration of buffer: | 100 mmole/l. in the test | |
|---|---|---|
| Concentration of the boron compound: | 120 mmole/l. in the test | |
| Buffer | non-specific agglutination ME/5 min. | % inhibition of non-spec. aggl. |
| | buffer | buffer + metaborate | |
| phosphate | 100 | 1 | 99 |
| HEPES | 229 | 1 | >99 |
| TRIS | 195 | 0 | 100 |
| metaborate | 106 | — | — |
| | buffer | buffer + boric acid | |
| phosphate | 189 | 136 | 28 |
| HEPES | 201 | 132 | 34 |
| TRIS | 161 | 44 | 73 |
| boric acid | 253 | — | — |
| | buffer | buffer + tetraborate | |
| phosphate | 100 | 0 | 100 |
| HEPES | 229 | 1 | >99 |
| TRIS | 195 | 1 | >99 |
| tetraborate | 0 | — | — |
| | buffer | buffer + perborate | |
| phosphate | 100 | 0 | 100 |
| HEPES | 229 | 2 | >99 |
| TRIS | 175 | 4 | 98 |
| perborate | 92 | — | — |

It can be seen that the non-specific agglutination in the case of the addition of the combination according to the present invention of a buffer with a boron compound inhibits up to 100%, whereas the addition of buffer or of a boron compound alone cannot remove the turbidity.

EXAMPLE 2

Several immuno-assays were carried out for the determination of TSH. In each case, tris buffer was used as buffer and the boron compound was varied. The procedure was substantially as described in Example 1 except that reagent 1 had the following composition:

70 mmole/liter buffer, pH 7.0
120 mmole/liter of boron compound
2% by weight PEG 6000
0.5% by weight Pluronic F68
1% by weight of bovine serum albumin
18 mmole/liter ethylenediamine-tetraacetic acid
10 mmole/liter sodium thiocyanate.

As antibodies, there were used polyclonal antibodies against TSH. The results obtained are given in the following Table 2.

TABLE 2

| Example: TSH determination | | |
|---|---|---|
| concentration of the buffer: | 70 mmole/l. in the test | |
| concentration of the boron compound: | 120 mmole/l. in the test | |
| buffer | non-specific agglutination mE/5 min. | % inhibition |
| | buffer | buffer + metaborate | |
| Tris | 142 | 76 | 47 |
| metaborate | 106 | — | — |
| | buffer | buffer + boric acid | |
| Tris | 120 | 10 | 92 |
| boric acid | 230 | — | — |
| | buffer | buffer + perborate | |
| Tris | 142 | 0 | 100 |
| perborate | 92 | — | — |

Here, too, it can be seen that a combination of tris buffer with borate leads to a practically complete suppression of the non-specific agglutination.

EXAMPLE 3

As described in Example 2, the non-specific agglutination in the case of the TSH determination with three different loading densities of polyclonal antibodies (100 µg, 200 µg and 400 µg antibody/mg latex) in the absence of borate and in the presence of borate in amounts increasing from 5 mmole to 150 mmole was measured. The results are shown in the drawing, which is a graph in which the non-specific agglutination mE/5min is plotted against the concentration of borate in mmole in 70 mmole TRIS.

It will be understood that the specification and examples are illustrative but not limitative of the present invention and that other embodiments within the spirit and scope of the invention will suggest themselves to those skilled in the art.

We claim:

1. In an immunoassay for determination of an immunologically active substance in a sample solution which contains non-specific agglutinations, wherein the immunologically active substance in the sample is reacted with a specific binding partner and the amount of bound specific binding partner is determined photometrically, wherein the improvement comprises removing said non-specific agglutinations by adding to the sample solution an inorganic boron compound selected from the group consisting of borates, metaborates, tetraborates and perborates, in sufficient amount to remove said agglutinations and in combination with a buffer system other than a boron buffer.

2. A process according to claim 1, in which the inorganic boron compound is added in an amount of from 100 to 150 mmole/liter and the buffer system is added in an amount of from 70 to 100 mmole/liter.

3. A process according to claim 2, wherein the buffer system is a zwitterionic buffer or a phosphate buffer.

4. A process according to claim 3, wherein the buffer system is a zwitterionic buffer which is tris or hepes buffer.

5. A process for the removal of non-specific agglutinations from a sample solution prior to determination of an immunologically active substance in the sample by photometric immunoassay, which comprises, prior to photometric determination, the step of adding to the sample solution a borate, metaborate, tetraborate or perborate in an amount of from 100 to 150 mmole/liter in combination with from 70 to 100 mmol/liter of a buffer system other than a boron buffer.

* * * * *

UNITED STATES PATENT AND TRADEMARK OFFICE
CERTIFICATE OF CORRECTION

PATENT NO. : 5,164,321
DATED : November 17, 1992
INVENTOR(S) : Dietmar Zdunek et al.

It is certified that error appears in the above-identified patent and that said Letters Patent is hereby corrected as shown below:

Column 3, line 20: change "20 120 mmole/litre" to -- 120 mmole/litre --.

Column 3, line 47, change "free of analyte. 80 pl of" to -- free of analyte --.

Signed and Sealed this

First Day of March, 1994

BRUCE LEHMAN

Attest:

Attesting Officer

Commissioner of Patents and Trademarks